US00PP10220P

United States Patent [19]

Mak

[11] Patent Number: Plant 10,220

[45] Date of Patent: Jan. 27, 1998

[54] LILY PLANT 'ALMA ATA'

[76] Inventor: Johan A. Mak, 5595 Halls Ferry Rd., Independence, Oreg. 97351

[21] Appl. No.: 687,004

[22] Filed: Jul. 18, 1996

[51] Int. Cl.[6] ..... A01H 5/00

[52] U.S. Cl. ..... Plt./87.4

[58] Field of Search ..... Plt./87.4

[56] References Cited

PUBLICATIONS

GTTM UPOVROM Citation for 'Alma Ata' NRP-BRLEL1023, Jul. 28, 1994.

*Primary Examiner*—James R. Feyrer

[57] ABSTRACT

A new variety of hybrid lily plant bearing large upright-facing flowers of excellent form and long persistence, both on the plant and as cut-flowers. The flowers of the new plant are particularly characterized by their pure white coloration, their lightly ruffled margins, their large size and substance, their upright to semi-upright orientation, and the sharply ascending pedicels of the upper flowers. This combination is completely new in the Oriental hybrid divisions of lilies suited to forcing and to mass commercial cultivation. The bulbs may be precooled and forced for cut-flower production.

1 Drawing Sheet

BACKGROUND OF THE INVENTION

My new variety of lily plant originated as a seedling which first flowered in't Zand, Netherlands, in 1988. The breeding efforts had as their objective the production Oriental hybrid lilies with upright or semi-upright white flowers without conspicuous spotting, suited to forcing into flower out of season, heretofore unknown in the lily breeding art.

I achieved the desired objective by intercrossing selected upright and semi-upright lightly spotted white Oriental seedlings selected for their suitability to forcing for year-round use as cut-flowers and carrying the recessive gene for a white coloration.

The flowers of my new lily are characterized by an upright orientation, large size and broad-tepalled "bowl-shaped" form, unusually thick substance, lightly ruffled tepal margins, and a distinctive pure white, unspotted coloration, unique among Oriental hybrid lilies. The pedicels of the upper flowers are ascending. The clone possesses unusually strong, stout stems. In addition, the clone possesses to a high degree desirable characteristics of hybrid vigor. The clone is a good grower and propagator, as observed at't Zand, Netherlands, and at Salem, Oreg.

My new variety of lily plant has been asexually reproduced by me and under my direction at't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, the ascending pedicels connecting the flower to the stem, and in particular the novel and distinctive flower form with lightly ruffled tepal margins, its upright to semi-upright orientation, and its pure white, unspotted coloration.

DESCRIPTION OF THE NEW VARIETY

The following is a detailed description of my new variety of Oriental hybrid lily, with nomenclature according to the

*International Lily Register* (Royal Horticultural Society of London, Second Edition, 1969), and with color designations according to the Colour Chart of The Royal Horticultural Society, published by the Society in 1966.

The Plant

Origin: Seedling.

Seed parent: Selected unnamed Oriental hybrid seedling.

Pollen parent: Selected unnamed Oriental hybrid seedling.

Commercial classification: Hybrid Lilium clone.

Horticultural classification: Division VII-B, bowl-shaped Oriental hybrid lily, according to the Horticultural Classification of Lilies, Royal Horticultural Society of London.

Form: Single stem, erect and stately.

Height: 70 to 100 cm from bulbs 14 to 18 cm in circumference, provided their light levels are adequate; low light levels may cause "stretching".

Growth: Vigorous and upright.

Foliage quantity: Abundant.

Size of leaf: Unusually broad, 4 to 7 cm wide×10 to 14 cm long.

Shape of leaf: Lanceolate (pointed).

Texture: Leathery and glossy.

Color: Medium green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 9 to 12 cm long and 10 to 14 cm in circumference just prior to opening.

Opening: Bud opens slowly, in response to morning light; this takes about one hour.

Color: Pure white.

Peduncle: Averages 4 to 6 cm, but it may elongate if light levels are too low or if bulbs have been improperly stored prior to forcing. Color is medium green with very light plum overlay.

The Flower

Blooming habit: Annually in midseason; flowers once and profusely.

Size: Flowers are large-sized, averaging 15 to 20 cm in diameter, reflexing at the tips on the second day to 15 to 17 cm in diameter. The tepals are broad: outer tepals are 2.5 to 3.25 cm wide, and the inner tepals are 4.5 to 5 cm wide.

Borne: In a single racemic inflorescence producing 4 to 8 flowers from a bulb 14 to 16 cm in circumference.

Shape: Form a broad bowl shape by the second day after opening, with the "bowl" 10 cm deep.

Tepalage: Typical of genus Lilium, with 6 imbricated tepals.

Tepal color: Pure white.

Tepal spotting: None.

Tepal longevity: Tepals stay on stems about three weeks.

Pedicel length: Average 8 to 12 cm long.

Pedicel color: Medium green with very light plum overlay.

Pedicel form: Sturdy and ascending, up to 60 degrees from the horizontal in the upper flowers.

Color changes: None.

Appearance: Flower is shiny.

Disease resistance: The flower and plant are resistant to disease; in particular, they are resistant to Fusarium bulb rot and Botryris blight.

Fragrance: Light sweet fragrance.

Lasting quality: The flower is long lasting, both on the plant and as a cut-flower.

The Reproductive Organs

Stamens: Arrangement typical of genus Lilium. Six stamens with soft green filaments 8 to 10 cm long.

Pollen and anthers (dehisced): R.H.S. CC greyed red 178A to 182 A.

Pistil: One in number, 8 to 10 cm long.

Stigma: Greyed purple R.H.S. CC 186 A-C/D, large in size.

Characteristics of ovary: Characteristic of genus Lilium.

The Fruit

Fertility: The fruit bears fertile seed.

Shape: Ovoid.

Color at maturity: Soft brown, sometimes overlaid with soft plum.

My new variety of Oriental hybrid lily most nearly resembles 'Casa Blanca,' but it has upfacing flowers with lightly raffled tepals. Its pedicels are more sharply ascending, and its inflorescence bears more flowers.

I claim:

1. A new and distinctive variety of Oriental hybrid lily plant substantially as herein shown and described, characterized by its versatility both as a garden plant and as a cut-flower producer from pre-cooled bulbs forced under glass out of season; and in particular by its unique upright to semi-upright flowers with ascending pedicels, its lightly ruffled tepal margins, and its pure white coloration, a combination unique among Oriental hybrid lilies suited to forcing and to mass commercial cultivation.

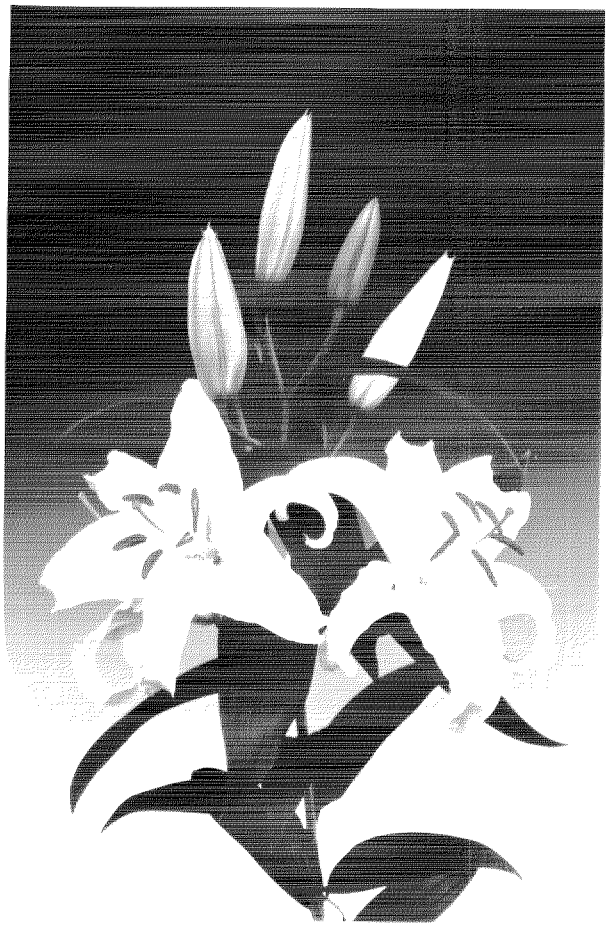

* * * * *